United States Patent
Majeed et al.

(10) Patent No.: US 9,610,273 B2
(45) Date of Patent: Apr. 4, 2017

(54) METHOD FOR THE TREATMENT OF HYPERCHOLESTEROLEMIA

(71) Applicant: SAMI LABS LIMITED, Bangalore (IN)

(72) Inventors: Muhammed Majeed, Edison, NJ (US); Kalyanam Nagabhushanam, East Windsor, NJ (US); Anju Majeed, Piscataway, NJ (US); Sarang Bani, Bangalore (IN); Anjali Pandey, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 87 days.

(21) Appl. No.: 14/637,081

(22) Filed: Mar. 3, 2015

(65) Prior Publication Data

US 2015/0306060 A1    Oct. 29, 2015

Related U.S. Application Data

(62) Division of application No. 14/259,404, filed on Apr. 23, 2014.

(51) Int. Cl.
*A61K 31/25* (2006.01)
*A61K 31/215* (2006.01)

(52) U.S. Cl.
CPC ............ *A61K 31/25* (2013.01); *A61K 31/215* (2013.01)

(58) Field of Classification Search
None
See application file for complete search history.

(56) References Cited

PUBLICATIONS

Kempaiah et al. in Journal of Nutritional Biochemistry 17, 471-278 (2006).*
Chempakam et al. in Chemistry of Spices, Chapter 6, 2008, Edited by V.A. Parthasarathy, B. Chempakam and T. John Zachariah.*
Park et al. in Journal of Natural Products 65(9), 1228-1231 (2002).*
Chen et al. in Disi Junyi Daxue Xuebao 30(1), 7-10 (2009) (Abstract).*
Law et al. in Am J Cardiol 2006; 97[suppl]:52C-60C.*
Oh et al. in Am Fam Physician. May 1, 2007;75(9):1365-1371.*
Chowdhury et al., "Effects of Turmeric and Garlic on Blood Cholesterol Level in Guinea Pig," Bangladesh J Pharmacol 2008; 3, 17-20.
Babu et al., "Hypolipidemic action of curcumin, the active principle of turmeric (*Curcuma longa*) in streptozotocin induced diabetic rats", Molecular and Cellular Biochemistry 166: 169-175, 1997.
Asma Ejaz et al., "Curcumin Inhibits Adipogenesis in 3T3-L1 Adipocytes and Angiogenesis and Obesity in C57/BL Mice1-3", The Journal of Nutrition and Disease, (2009), pp. 919-925.

* cited by examiner

*Primary Examiner* — Dennis Heyer
(74) *Attorney, Agent, or Firm* — Oliff PLC

(57) ABSTRACT

Disclosed is a therapeutic management method of hypercholesterolemia in mammals. More specifically, the present invention relates to a method of reducing high levels of circulating cholesterol (hypercholesterolemia) in the blood stream of mammals, said method involving step of administering therapeutically effective amounts of Calebin A to said mammals to bring about the effects of (i) reducing the amount of total blood cholesterol levels; (ii) reducing the concentrations of low density lipoproteins (LDL) and very low density lipoproteins (VLDL); (iii) increasing the concentrations of high density lipoproteins (HDL) and (iv) reducing concentrations of serum triglycerides.

2 Claims, No Drawings

METHOD FOR THE TREATMENT OF HYPERCHOLESTEROLEMIA

CROSS REFERENCE TO RELATED APPLICATIONS

This patent application is a divisional of co-pending U.S. application Ser. No. 14/259,404 filed 23 Apr. 2014 which is included herein in its entirety.

FIELD OF THE INVENTION

The invention in general relates to therapeutic management methods for hypercholesterolemia. More specifically, the present invention relates to the management of hypercholesterolemia in mammalian subjects using therapeutically effective amounts of Calebin A.

BACKGROUND OF THE INVENTION

Description of Prior Art

Hypercholesterolemia is a condition characterized by very high levels of cholesterol in the blood. The common medical causes of hypercholesterolemia include,
1. Carcinoma, hepatocellular;
2. Hypertriglyceridemia;
3. Familial hypercholesterolemia;
4. Coronary artery disease;
5. Diabetes mellitus;
6. Nephritic syndrome;
7. Zieve's syndrome;
8. Anorexia nervosa;
9. Lack of physical activity;
10. Obesity; and
11. Diet rich in saturated fat While the human body requires cholesterol for multifarious functions like building cell membranes, making hormones, and producing, fat digestive compound, excessive cholesterol increases a person's risk of developing heart disease. People with hypercholesterolemia have a high risk of developing a form of heart disease called "atherosclerotic heart disease" or "coronary artery disease" were excess cholesterol in the bloodstream is deposited in the walls of blood vessels, particularly in the arteries that supply blood to the heart (coronary arteries). The abnormal buildup of cholesterol forms clumps (plaque) that narrow and harden artery walls. As the clumps get bigger, they can clog the arteries and restrict the flow of blood to the heart. The buildup of plaque in coronary arteries causes a form of chest paw called angina and greatly increases a person's risk of having a heart attack. In general optimized cholesterol metabolism is required for healthy living. Cholesterol travels through the bloodstream in small packages called lipoproteins. Two kinds of lipoproteins carry cholesterol throughout the body: low-density lipoproteins (LDL) and high-density lipoproteins (HDL). Having healthy levels of both types of lipoproteins is important LDL cholesterol sometimes is called "bad" cholesterol. A high LDL level leads to a buildup of cholesterol in arteries, HDL cholesterol sometimes is called "good" cholesterol. This is because it carries cholesterol from other parts of your body back to your liver. The liver then removes the cholesterol from your body. Effective therapeutic management methods for hypercholesterolemia aim to reduce LDL cholesterol and increase levels of HDL cholesterol so that excess cholesterol may be removed efficiently from the body.

Accordingly, it is the principle objective of the present invention to disclose method of therapeutically managing hypercholesterolemia in mammals using therapeutically effective amounts of Calebin A.

The present invention fulfills the principle objective and provides related advantages.

SUMMARY OF THE INVENTION

Disclosed is a therapeutic management method of hypercholesterolemia in mammals. More specifically, the present invention relates to a method of reducing high levels of circulating cholesterol (hypercholesterolemia) in the blood stream of mammals, said method involving step of administering therapeutically effective amounts of Calebin A to said mammals.

DESCRIPTION OF THE MOST PREFERRED EMBODIMENTS

In the most preferred embodiments, the present invention relates to the following.

We claim,
1. A method of reducing high levels of circulating cholesterol (hypercholesterolemia) in mammalian blood, said method involving step of orally administering therapeutically effective amounts of Calebin A to said mammals to achieve the effect of reducing the concentration of total cholesterol in the blood.
2. A method of treating hypercholesterolemia in mammals, said method involving step of orally administering therapeutically effective amounts of Calebin A to bring about effects of (i) reducing the concentrations of low density lipoproteins (LDL) and very low density lipoproteins (VLDL) and (ii) increasing the concentrations of high density lipoproteins (HDL) in the blood of said mammals.
3. A method of reducing high levels of serum triglycerides in mammals, said method involving the step of orally administering therapeutically effective amounts of Calebin A to mammals in need of such reduction.
4. A method for aiding in preventing, delaying the onset of and/or slowing the progression of atherosclerosis in a mammal, said method comprising step of orally administering therapeutically effective amounts of Calebin A to said mammal, to achieve (i) a reduction in the concentration of low density lipoproteins (LDL) and very low density lipoproteins (VLDL) and (ii) an increase in the concentration of High Density Lipoproteins (HDL) in the blood.
5. A method of aiding in preventing delaying the onset of and/or slowing the progression of hypertriglyceridemia induced fatty liver author pancreatitis in a mammal, said method comprising step of orally administering therapeutically effective amounts of Calebin A to said mammal to bring about the effect of reducing serum triglyceride concentration.
6. Calebin A for use in treating hypercholesterolemia in mammals wherein the effect of reducing the amount of total blood cholesterol levels is achieved in said mammals by the oral administration of therapeutically effective amounts of Calebin A.
7. Calebin A for use in treating hypercholesterolemia in mammals wherein the effects of (i) reducing the concentrations of low density lipoproteins (LDL) and very low density lipoproteins (VLDL) and (ii) increasing the concentrations of high density lipoproteins (HDL) in the blood of said mammals is achieved by the oral administration of therapeutically effective amounts of Calebin A.

8. Calebin A for use in treating serum hypertriglyceridemia in mammals wherein the effect of reducing the concentrations of serum triglycerides in said mammals is achieved by the oral administration of therapeutically effective amounts of Calebin A.

9. Use of Calebin A in a therapeutic method for treating hypercholesterolemia in mammals wherein the effect of reducing the amount of total blood cholesterol levels is achieved in said mammals by the step of orally administering therapeutically effective amounts of Calebin A.

10. Use of Calebin A in a therapeutic method for treating hypercholesterolemia in mammals wherein the effects of (i) reducing the concentrations of low density lipoproteins (LDL) and very low density lipoproteins (VLDL) and (ii) increasing the concentrations of high density lipoproteins (HDL) in the blood of said mammals is achieved by step of orally administering therapeutically effective amounts of Calebin A.

11. Use of Calebin A in a therapeutic method for treating serum hypertriglyceridemia in mammals wherein the effect of reducing concentrations of serum triglycerides in said mammals is achieved by step of orally administering therapeutically effective amounts of Calebin A.

The detailed description of the preferred embodiments as specified herein above is further substantiated by illustrative examples set forth below.

Example 1

Acute Oral Toxicity of Calebin A

Table I lists the parameters studied for Acute Oral Toxicity of Calebin A.

Results:

No mortality was observed up to 2000 mg/kg p.o. in mice up to two weeks of observation.

TABLE I

Parameters studied for Acute Oral Toxicity of Calebin A

| General Behaviour | Dermal |
|---|---|
| Aggression = Nil<br>Fear = Nil<br>Passive = Nil<br>General Movement = Normal<br>General Locomotor Activity = Normal | Blanching = Nil<br>Hyperaemia = Nil<br>Cyanosis = Nil |

| Central Nervous System | General Parameters |
|---|---|
| Excitation = Nil<br>Motor Activity = Nil<br>Tremors = Nil<br>Clonic Convulsions = Nil<br>Tonic Convulsion = Nil | Muscular Weakness = Nil<br>Salivation = Nil<br>Pilo Erection = Nil<br>Diarrhea = Nil |

| Respiratory System | Reflexes |
|---|---|
| Respiration Rate = Normal<br>Respiration Depth = Normal | Corneal = No effect<br>Pinnal = No effect |

| Autonomic Nervous System | Food and Water (Intake and Excretion) |
|---|---|
| Motor Activity = Normal<br>Atexia = Nil<br>Respiration Rate = Normal<br>Diarrhea = Nil | Fecal Output = Normal<br>Urine Output = Normal |

Animal Experiment for demonstrating the effect of Calebin A in treating hypercholesterolemia and hyperlipidemia.

Test System Details

1. Animal species: Mice.
2. Strain: C57.
3. Source: In-House
4. Body weight range
5. Males - 22.1-25.8 g
6. Females - 20.3-23.9 g
7. Age at treatment: 8-10 weeks
8. Number of Groups: 5 groups (One Control, One High fat diet control and three treatment groups)
9. Number of animals/group: Each group consists of 10 animals (5 Males + 5 Females). Female animals used were nulliparous and non-pregnant
10. Total number of animals: 50
11. Identification: Cage cards and individual animal ear notching method.
12. Experimental condition: Obesity as a risk factor for hypercholesterolemia and hyperlipidemia Test Performance A. Husbandry a. Conditions: The animals were housed under standard laboratory conditions, air-conditioned with adequate fresh an supply (Air changes 12-15 per hour), room temperature 22±3° C., relative humidity 30-70% with 12 hours light and 12 hours dark cycle. The temperature and relative humidity are recorded once daily.

b. Housing: Individual animals were housed in a standard polypropylene cage Size: L 290×B 140×H 140 mm) with stainless steel mesh top grill having facilities for holding pellet feed and drinking water in water bottle fitted with stainless steel sipper tube. Clean sterilized paddy husk is provided as bedding material.

c. Acclimatization: The animals were acclimatized for 5 days to laboratory conditions and were observed for clinical signs daily.

d. Diet: The animals were fed ad libitum with AMRUT Laboratory Animal feed manufactured by Pranav Agro Industries Limited, Sangli, Maharastra throughout the acclimatization Open Source Diet D12450B diet (with 10 kcal % Fat) and Open Source Diet D12492 High fat diet (with 60 kcal % Fat) manufactured by Research Diet Inc, USA procured from Indus Marketing, Hyderabad, Andhra Pradesh, INDIA was used for induction of obesity and the main study.

e. Water: Clean drinking water was provided ad libitum throughout the acclimatization and obesity induction period. Deep bore-well water passed through reverse osmosis unit was provided in plastic water bottles with stainless steel sipper tubes.

B. Grouping

Grouping of animals was done on the last day of acclimatization by body weight randomization and stratification method. Grouping of animals was done such that body weight variation of animals used does not exceed±20% of the mean body weight of each group.

C. Study Design

The animals were divided into 5 groups viz., Group 1, 2, 3, 4 and 5 consisting of 10 animals (5 male and 5 female) each. The group details, doses and number/sex of animals per group are presented in Table II.

TABLE II

| Group | Treatment | Dose (mg/kg Bwt) | Number of Animals Male | Number of Animals Female | Animal numbers Male | Animal numbers Female |
|---|---|---|---|---|---|---|
| G1 | Control (with 10 kcal % Fat) | — | 5 | 5 | 1-5 | 26-10 |
| G2 | High fat diet Control (with 60 kcal % Fat) | — | 5 | 5 | 6-10 | 31-35 |
| G3 | Calebin A 5 mg/kg + High fat diet (with 60 kcal % Fat) | 5 | 5 | 5 | 11-15 | 36-40 |
| G4 | Calebin A 10 mg/kg + High fat diet (with 60 kcal % Fat) | 10 | 5 | 5 | 16-20 | 41-45 |
| G5 | Calebin A 20 mg/kg + High fat diet (with 60 kcal % Fat) | 20 | 5 | 5 | 21-25 | 46-50 |
| | Total: | | 25 | 25 | — | — |
| | Total number of animals: | | | 50 | | |

D. Animal Treatment a. Dose Volume: Dose volume/animal=10 ml/kg body weight for all animals throughout the study period b. Obesity induction: The G1 Control group animals were fed with normal control diet feed D12450B containing 10 kcal % fat and the G2 to G5 group animals were fed with high fat diet feed D12492 containing 60 kcal % fat during the induction of obesity and during main study. Obesity induction was done considering the scientific rationale that obesity is a serious risk factor for hypercholesterolemia.

c. Main Study: The main study was started after the induction of obesity. The 3 doses of Calebin A was administered to animals from Day 29 daily consecutively for a period of 28 days. The feeding of diets continued in the main study in a similar way as performed in induction of obesity. The G1 Control and G2 High fat diet control group animals were administered with 0.5% CMC (Carboxy Methyl Cellulose) while other group animals received test item from Day 29 to Day 56 of the study period. The dose volume of administration was maintained according to the weekly body weight of individual animals.

d. Duration of the study: The total duration of the study was 61 days (5 days Acclimatization period+28 days Induction of obesity+26 days Main study).

Statistical Analysis and Report Preparation

The raw data obtained from the present study were subjected to computer statistical processing. The computer printout of the data (in the form of appendix) was verified with the original raw data. After verification, the data was subjected to One-way ANOVA (Analysis of Variance) with Dunnett's post test for the data on body weights, hematology and clinical chemistry parameters, organ weights using GraphPad Prism version 5.01, GraphPad Software. All analyses and comparisons was evaluated at the 95% level of confidence (P<0.05), indicated by the designated by the superscripts of a where G1 is compared to G3, G4, G5, and G6 and b where G2 is compared to G3, G4, G5, and G6 throughout the report as stated below: *: Statistically significant (P<0.05) wherever applicable.

The data were subjected to One way—ANOVA statistical analysis by comparing following:

G1 group {Control group (with 10 kcal % Fat)} to G3 group {Calebin A 5 mg/kg+High fat diet (with 60 kcal % Fat)}, G4 group {Calebin A-10 mg/kg+High fat diet (with 60 kcal % Fat)} and G5 group {Calebin A-20 mg/kg+High fat diet (with 60 kcal % Fat)} as represented below:

| G1 group Control group (with 10 kcal % Fat) | G3 group Calebin A-5 mg/kg + High fat diet (with 60 kcal % Fat) G4 group Calebin A-10 mg/kg + High fat diet (with 60 kcal % Fat) G5 group Calebin A-20 mg/kg + High fat diet (with 60 kcal % Fat) |
|---|---|

G2—High fat diet Control (with 60 kcal % Fat) to G3 group {Calebin A-5 mg/kg+High fat diet (with 60 kcal % Fat)}, G4 group {Calebin A-10 mg/kg+High fat diet (with 60 kcal % Fat)} and G5 group {Calebin A-20 mg/kg High fat diet (with 60 kcal % Fat)} as represented below:

| G2 group High fat diet Control (with 60 kcal % Fat) | G3 group Calebin A-5 mg/kg + High fat diet (with 60 kcal % Fat) G4 group Calebin A-10 mg/kg + High fat diet (with 60 kcal % Fat) G5 group Calebin A-20 mg/kg + High fat diet (with 60 kcal % Fat) |
|---|---|

Results (Tables IV, IV (a), V, V (a))

At the completion of the study period, blood samples were collected from all the animals in tubes containing potassium ethylene di-amide tetra acetic acid (K2-EDTA) anticoagulant for hematology and without anticoagulant for clinical chemistry. The blood samples collected in tubes without anticoagulant were centrifuged at 3000 rpm for 10 minutes to obtain serum. Blood samples were collected humanely from retro-orbital plexus puncture method under mild ether anesthesia with the help of a fine capillary tube. The following clinical chemistry parameters were analyzed.

The following clinical chemistry parameters (TABLE III) were analyzed using the "Erba Mannheim Chem Touch analyzer" (Transasia Bio-Medicals Ltd, India) from serum samples.

| Parameters | Units |
|---|---|
| Total Protein | g/dL |
| Albumin | g/dL |
| Glucose | mg/dL |
| Alanine aminotransferase (ALT) | IU/L |

| Parameters | Units |
|---|---|
| Aspartate aminotransferase (AST) | IU/L |
| Triglycerides | mg/dL |
| Total Cholesterol | mg/dL |
| High Density Lipoproteins (HDL) | mg/dL |
| Very Low Density Lipoproteins (VLDL) | mg/dL |
| Low Density Lipoproteins (LDL) | mg/dL |

TABLE IV

CLINICAL CHEMISTRY PARAMETERS (Male animals)

| Group | Treatment | Total Protein | Albumin | Glucose | ALT/SGPT | AST/SGOT | Triglycerides | Total Cholesterol |
|---|---|---|---|---|---|---|---|---|
| G1[a] | Control (with 10 kcal % Fat) | 5.05 ± 0.59 | 2.74 ± 0.14 | 144.40 ± 11.46 | 75.67 ± 24.15 | 85.22 ± 27.88 | 81.94 ± 12.97 | 53.32 ± 16.84 |
| G2[b] | High fat diet Control (with 60 kcal % Fat) | 4.88 ± 0.56 | 2.71 ± 0.60 | 133.35 ± 58.39 | 71.07 ± 34.80 | 117.74 ± 34.52 | 96.85 ± 10.60 | 104.84 ± 40.97 |
| G3 | Calebin A 5 mg/kg + High fat diet (with 60 kcal % Fat) | 4.74 ± 0.23 | 2.73 ± 0.23 | 159.30 ± 17.02 | 64.35 ± 24.58 | 86.99 ± 35.22 | 76.53 ± 17.11 | 63.46 ± 16.64 |
| G4 | Calebin A 10 mg/kg + High fat diet (with 60 kcal % Fat) | 5.08 ± 0.49 | 2.43 ± 0.42 | 130.49 ± 21.28 | 54.81 ± 13.58 | 89.48 ± 35.58 | 65.15**[b] ± 10.43 | 61.86*[b] ± 21.26 |
| G5 | Calebin A 20 mg/kg + High fat diet (with 60 kcal % Fat) | 4.42 ± 0.48 | 2.66 ± 0.17 | 105.89 ± 37.17 | 48.44 ± 9.73 | 90.17 ± 25.87 | 62.35**[b] ± 14.20 | 70.48 ± 14.59 | n = 5;
Values - Mean ± Standard Deviation;
P < 0.05

TABLE IV (a)

CLINICAL CHEMISTRY PARAMETERS (Male animals)

| Group | Treatment | HDL (mg/dl) | VLDL (mg/dl) | LDL (mg/dl) |
|---|---|---|---|---|
| G1[a] | Control (with 10 kcal % Fat) | 27.19 ± 14.72 | 10.66 ± 3.37 | 77.68 ± 8.14 |
| G2[b] | High fat diet Control (with 60 kcal % Fat) | 32.07 ± 14.01 | 20.97 ± 8.19 | 100.61 ± 15.44 |
| G3 | Calebin A 5 mg/kg + High fat diet (with 60 kcal % Fat) | 20.46 ± 15.67 | 12.69 ± 3.33 | 85.55 ± 20.87 |
| G4 | Calebin A 10 mg/kg + High fat diet (with 60 kcal % Fat) | 41.80 ± 21.20 | 12.37*[b] ± 4.25 | 97.45 ± 23.49 |
| G5 | Calebin A 20 mg/kg + High fat diet (with 60 kcal % Fat | 47.26 ± 29.34 | 14.10 ± 2.92 | 94.46 ± 18.38 | n = 5;
Values - Mean ± Standard Deviation;
P < 0.05

TABLE V

CLINICAL CHEMISTRY PARAMETERS (Female animals)

| Group | Treatment | Total Protein | Albumin | Glucose | ALT/SGPT | AST/SGOT | Triglycerides | Total Cholesterol |
|---|---|---|---|---|---|---|---|---|
| G1[a] | Control (with 10 kcal % Fat) | 4.81 ± 0.20 | 2.90 ± 0.26 | 107.03 ± 38.92 | 68.60 ± 14.86 | 77.79 ± 27.59 | 60.79 ± 7.33 | 65.18 ± 15.95 |
| G2[b] | High fat diet Control (with 60 kcal % Fat) | 4.70 ± 0.34 | 2.90 ± 0.18 | 123.04 ± 19.04 | 38.05 ± 10.32 | 99.71 ± 34.93 | 63.70 ± 11.62 | 64.56 ± 23.24 |
| G3 | Calebin A 5 mg/kg + High fat diet (with 60 kcal % Fat) | 5.37 ± 0.80 | 2.82 ± 0.19 | 134.52 ± 26.85 | 41.73 ± 5.39 | 80.51 ± 32.35 | 60.15 ± 10.25 | 75.71 ± 13.90 |
| G4 | Calebin A 10 mg/kg + High fat diet (with 60 kcal % Fat) | 4.91 ± 0.20 | 2.80 ± 0.38 | 112.34 ± 11.35 | 63.29 ± 32.86 | 79.89 ± 50.05 | 59.70 ± 4.33 | 47.54 ± 14.21 |
| G5 | Calebin A 20 mg/kg + High fat diet (with 60 kcal % Fat) | 4.88 ± 0.27 | 2.35***[b] ± 0.45 | 93.58 ± 11.49 | 55.51 ± 16.94 | 79.91 ± 36.82 | 52.88 ± 4.56 | 69.14 ± 21.88 | n = 5;
Values - Mean ± Standard Deviation;
P < 0.05

TABLE V (a)

CLINICAL CHEMISTRY PARAMETERS (Female animals)

| Group | Treatment | HDL (mg/dl) | VLDL (mg/dl) | LDL (mg/dl) |
|---|---|---|---|---|
| G1[a] | Control (with 10 kcal % Fat) | 68.11 ± 37.46 | 13.04 ± 3.19 | 59.19 ± 9.99 |
| G2[b] | High fat diet Control (with 60 kcal % Fat) | 64.97 ± 36.66 | 12.91 ± 4.65 | 90.30 ± 24.98 |
| G3 | Calebin A 5 mg/kg + High fat diet (with 60 kcal % Fat) | 81.59 ± 51.69 | 15.14 ± 2.78 | 78.68 ± 17.68 |
| G4 | Calebin A 10 mg/kg + High fat diet (with 60 kcal % Fat) | 66.85 ± 39.10 | 9.51 ± 2.84 | 61.20*[b] ± 12.22 |
| G5 | Calebin A 20 mg/kg + High fat diet (with 60 kcal % Fat | 66.67 ± 44.62 | 13.83 ± 4.38 | 52.31**[b] ± 11.11 | n = 5;
Values - Mean ± Standard Deviation;
P < 0.05

Interpretation of Results:

Clinical chemistry parameters statistical analysis comparison between G1 to G3, G4, G5, and G6

Albumin

In female animals, there was statistically significant decrease in mean Albumin values of G5 group {Calebin 20 mg kg+High fat diet (with 60 kcal % Fat)} compared to G1 group {Control group (with 10 kcal % Fat)}. These changes can be considered as incidental as there was no dose dependent response.

Clinical chemistry parameters statistical analysis comparison between G2 to G3, G4, G5, and G6

Triglycerides

In male animals, there was decrease in mean Triglycerides values of G3 group {Calebin A-5 mg/kg+High Fat diet (with 60 kcal % Fat)}, G4 group {Calebin A-10 mg/kg+High fat diet (with 60 kcal % Fat)}, G5 group {Calebin A-20 mg/kg+High fat diet (with 60 kcal % Fat)} compared to G2 group High fat diet Control (with 60 kcal % Fat). This decrease in mean Triglycerides value changes could be due to the effect of the test item Calebin A.

Total Cholesterol

In male animals, there was decrease in mean Total Cholesterol values of G3 group {Calebin A-5 mg/kg+High fat diet (with 60 kcal % Fat)} G4 group {Calebin A-10 mg/kg+High fat diet (with 60 kcal % Fat)}, G5 group {Calebin A-20 mg/kg+High fat diet (with 60 kcal % Fat)} compared to G2 group High fat diet Control (with 60 kcal % Fat). This decrease in mean Total Cholesterol value changes could be due to the effect of test item Calebin A.

Albumin in female animals, there was statistically significant decrease in mean Albumin values of G5 group {Calebin A-20 mg/kg+High fat diet (with 60 kcal % Fat)} compared to G2 group High fat diet Control (with 60 kcal % Fat). These changes can be considered as incidental as there was no dose dependent response.

Low Density Lipoproteins

In male and female animals, there was decrease in mean Low Density Lipoproteins values of G3 group {Calebin A-5 mg/kg+High fat diet (with 60 kcal % Fat)} G4 group {Calebin A-10 mg/kg High fat diet (with 60 kcal % Fat)}, G5 group {Calebin A-20 mg/kg+High fat diet (with 60 kcal % Fat)} compared to G2 group High fat diet Control (with 60 kcal % Fat). This decrease in mean low density lipoprotein values changes could be due the effect of the test item Calebin A.

High Density Lipoproteins

In male and female animals, there was increase in mean high Density Lipoproteins values of G4 group {Calebin A-10 mg/kg+High fat diet (with 60 kcal % Fat)}, G5 group {Calebin A-20 mg/kg+High fat diet (with 60 kcal % Fat)} compared to G2 group High fat diet Control (with 60 kcal % Fat). This increase in mean high density lipoprotein values changes could be due the effect of the test item Calebin A.

Very Low Density Lipoproteins

In male and female animals, there was decrease in mean Very Low Density Lipoproteins values of G3 group {Calebin A-5 mg/kg+High fat diet (with 60 kcal % Fat)} G4 group {Calebin A-10 mg/kg High fat diet (with 60 kcal % Fat)}; G5 group {Calebin A-20 mg/kg+High fat diet (with 60 kcal % Fat)} compared to G2 group High fat diet Control (with 60 kcal % Fat). This decrease in mean very low density lipoprotein values changes could be due the effect of the test item Calebin A Conclusion: Calebin A at effective concentration doses of 5, 10 and 20 mg/kg body weight (i) decreased LDL and VLDL concentrations in the blood of hypercholesterolemic mammals; (ii) increased HDL concentrations in the blood of hypercholesterolemic mammals and (iii) lowered serum triglyceride concentrations in the blood of hyperlipidemic mammals.

While the invention has been described with reference to a preferred embodiment, it is to be clearly understood by those skilled in the art that the invention is not limited thereto. Rather, the scope of the invention is to be interpreted only in conjunction with the appended claims.

Calebin-A naturally occurs in some *Curcuma* species along with two isomeric forms of Demethoxy-Calebin A and a single isomer of Bis-Demethoxy Calebin A. These three analogs of Calebin A occur in minute quantities. But they share many of the properties of Calebin A to a large extent depending on the test system. Hence the claims on the uses of Calebin A very well extend to these natural s and synthetic analogs also.

We claim:

1. A method of reducing high levels of serum triglycerides in mammals, said method comprising a step of orally administering to a male mammal in need thereof a therapeutically effective amount of Calebin A to achieve the effect of reducing the concentration of serum triglycerides in the blood, wherein the therapeutically effective amount of Calebin A is a Calebin A concentration of 10 mg/kg body weight, and the medical cause of the high levels of serum triglycerides is obesity.

2. The method of claim 1, wherein the mammal is a mammal in need of the reduction of high levels of circulating cholesterol in mammalian blood, and the step of orally administering the therapeutically effective amount of Calebin A also achieves the effect of reducing the concentration of total cholesterol in the blood.

* * * * *